US00PP37598P2

(12) United States Plant Patent
Hansen

(10) Patent No.: US PP37,598 P2
(45) Date of Patent: Aug. 18, 2026

(54) *VEONICA* PLANT NAMED 'Jedi Gem'

(50) Latin Name: *Veronica spicata*
Varietal Denomination: Jedi Gem

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,998

(22) Filed: Jan. 14, 2026

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./263.1, 251
See application file for complete search history.

(56) References Cited

U.S. PATENT DOCUMENTS

PP29,681 P3 * 9/2018 Hansen ..... A01H 6/00
Plt./251

* cited by examiner

*Primary Examiner* — Karen M Redden

(57) ABSTRACT

A new and distinct cultivar of ornamental Spiked Speedwell, *Veronica spicata* plant named 'Jedi Gem', with dense medium-height habit, stiff, upright, heavily-branched spikes of densely-arranged medium pink flowers beginning in early summer and continuing for twelve to fourteen weeks above clean, dark-green, lanceolate, highly lustrous foliage maintained through the growing season. The new plant is useful in the landscape as a specimen, en masse, as a container plant, or as a cut flower, and maintains its foliage through the season with good disease tolerance, specifically rust resistance.

2 Drawing Sheets

Botanical classification: *Veronica spicata.*
Variety denomination: 'Jedi Gem'.

STATEMENT REGARDING PRIOR DISCLOSURES UNDER 37 CFR 1.77(b)(6)

*Veronica* 'Jedi Gem' was first privately offered for sale to Down to Earth Nursery by Walters Gardens, Inc. on Jan. 21, 2025. Subsequently, on Feb. 1, 2025, the new plant was posted on a website operated by Walters Gardens, Inc. and on Jun. 3, 2025, the new plant was described with a photograph in the "Walters Gardens 2025-2026 Catalog" by Walters Gardens, Inc. Walters Gardens, Inc. obtained the plant and all information relating thereto, from the inventor. No plants of *Veronica* 'Jedi Gem' have been sold or offered for sale in this country or anywhere in the world, nor has any disclosure of the new plant been made more than one year prior to the filing date of this application and such sale or disclosure within one year was either derived directly or indirectly from the inventor and would be a 35 U.S.C § 102b exception.

BACKGROUND OF THE INVENTION

The present invention relates to the new and distinct cultivar of Spiked Speedwell, botanically known as *Veronica* 'Jedi Gem' and hereinafter referred to by the cultivar name or as the "new plant". The new plant was selected as a whole plant mutation of 'Purple Leia' U.S. Plant Pat. No. 34,278 in the summer of 2021 at a wholesale perennial nursery in Zeeland, Michigan, USA. During the evaluation period the new plant was assigned the code 21-Sp-Vern-1078 until the cultivar name was used.

'Jedi Gem' has been asexually propagated initially by division and later by basal cuttings and shoot tip tissue culture at the same nursery in the greenhouses in Zeeland, MI, since the summer of 2022 with subsequent asexually propagated plants found to be identical to the original selection with all the same traits as the original seedling though multiple generations.

BRIEF SUMMARY OF THE PLANT

*Veronica* 'Jedi Gem' is unique from all other Spiked Speedwell known to the inventor. Several other cultivars may have some similar traits, but this is the only variety known by the inventor to have the following characteristic combinations that establish the new plant as unique:

1. Dense, medium-height with stiff, upright spikes above thick stems of dark-green foliage;
2. Flowering in numerous spikes with densely-arranged medium pink flowers;
3. Dark-green, clean, highly lustrous, lanceolate foliage;
4. Heavily-branched spikes begin blooming in early summer and continue for twelve to fourteen weeks into early autumn;
5. Maintains foliage through the season.

The closest comparison varieties known to the inventor are: 'Allchoice' U.S. Plant Pat. No. 27,257, 'Allkiss' U.S. Plant Pat. No. 28,797, 'Giles van Hees' (not patented), 'Perfectly Picasso' U.S. Plant Pat. No. 29,720, 'Pink Bomb' U.S. Plant Pat. No. 24,756, 'Pink Explosion' U.S. Plant Pat. No. 22,592, 'Pink Eveline' U.S. Plant Pat. No. 18,743, 'Pink Marshmallow' (not patented), 'Pink Passion' U.S. Plant Pat.

No. 32,360, 'Pink Potion' U.S. Plant Pat. No. 29,681, 'Sweet Lullaby' U.S. Plant Pat. No. 23,611, and 'Tickled Pink' U.S. Plant Pat. No. 16,182.

'Allchoice' has a shorter habit and produces lighter pink flowers. 'Allkiss' is shorter and narrower in habit, the leaves are slightly shorter, and has a flower color is more purplish-red to purplish-pink and lightens to a pale purplish-pink. 'Giles van Hees' has a much shorter habit, the peduncles are less branched, and the flowers are more reddish-pink on shorter peduncles. 'Perfectly Picasso' has a slightly shorter habit and the flowers are a violet-purple. 'Pink Bomb' has a shorter and narrower habit, with lighter pink flowers. 'Pink Explosion' has a shorter habit with flowers that are very pale purple. 'Pink Eveline' has a habit that is about half as tall with shorter inflorescences. 'Pink Marshmallow' has a shorter habit and deeper pink flower color that fades less with maturity. 'Pink Passion' has a much shorter habit and more vivid purplish-red flower color. 'Pink Potion' has a shorter habit and distinct flower color. 'Sweet Lullaby' has a much shorter habit and the flower color is a lighter purplish-pink. 'Tickled Pink' has a more prostrate habit with shorter inflorescences that are a strong purplish-pink.

The parent plant has a similar habit with flowers that are rosy-purple.

BRIEF DESCRIPTION OF THE DRAWINGS

The photographs of the new plant demonstrate the overall appearance and unique traits of 'Jedi Gem' as two-year-old plants grown in a full-sun display garden in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
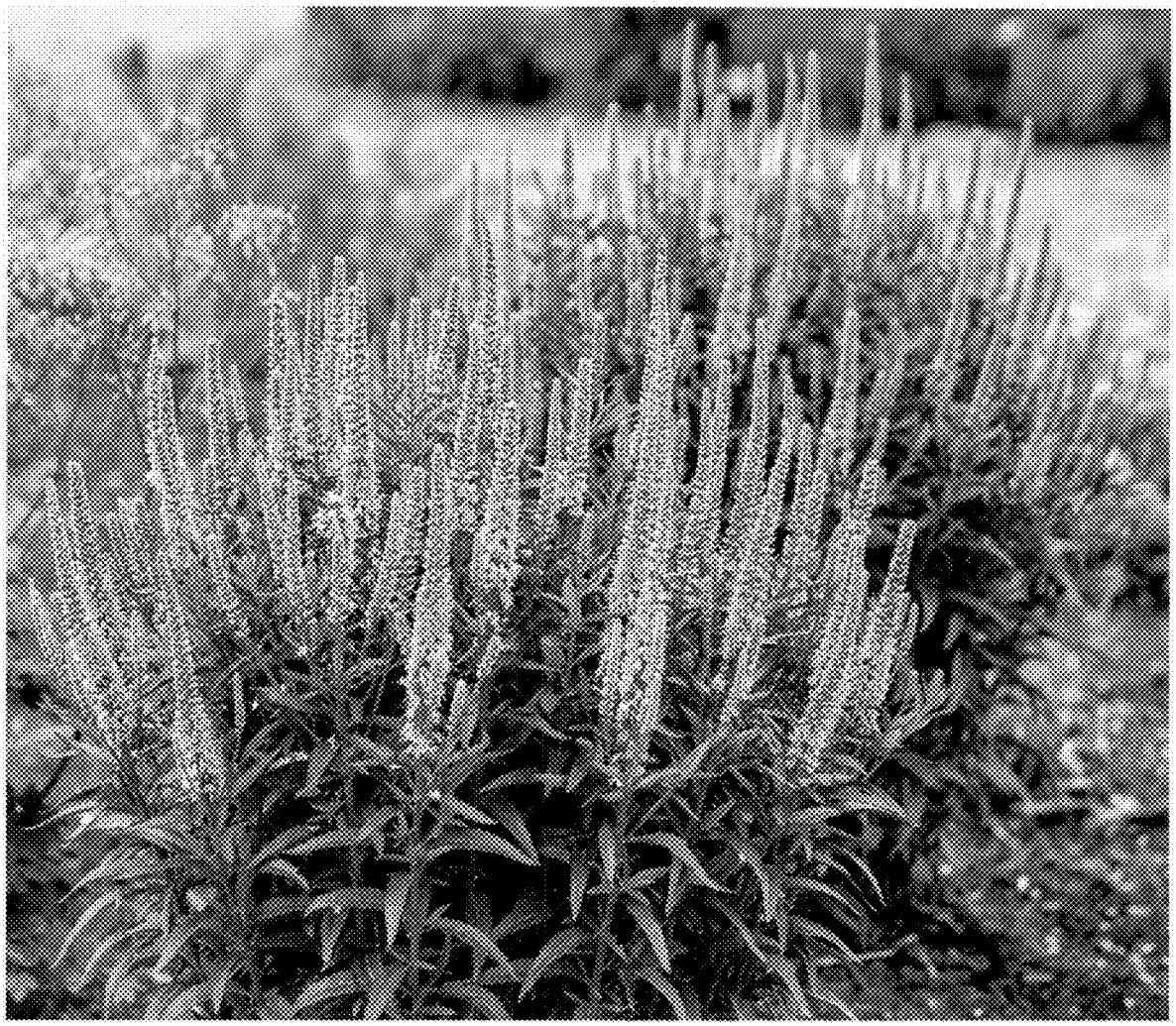
FIG. 1 shows a row of the new plants in early full flower.
Figure 2:
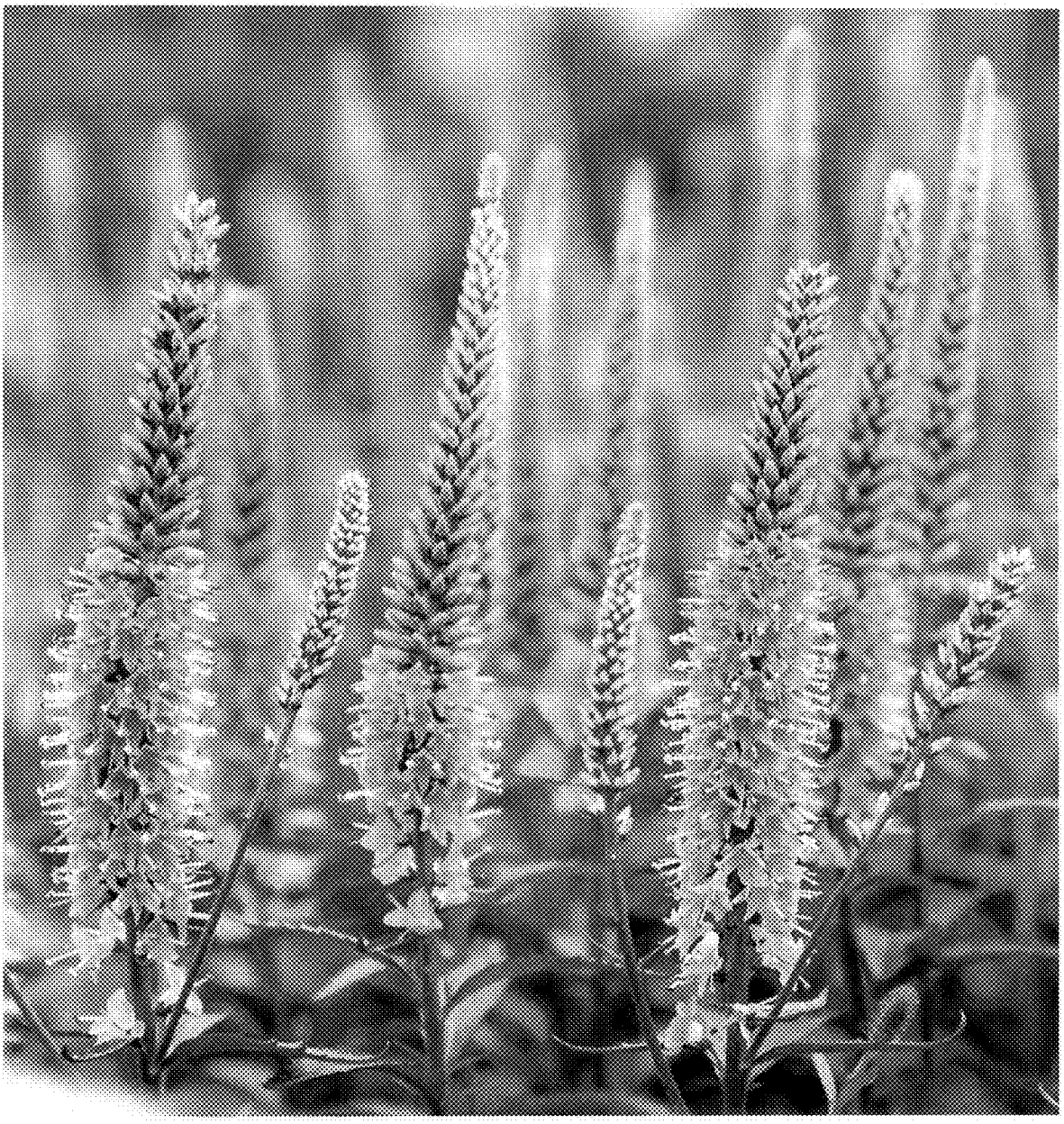
FIG. 2 shows a close-up of the flowers and buds.

The following descriptions and color references of *Veronica* 'Jedi Gem' are based on the 2015 edition of The Royal Horticultural Society Colour Chart except where common dictionary terms are used. 'Jedi Gem' has not been observed under all possible environments. The phenotype may vary slightly with different growing environments such as temperature, light, fertility, soil pH, moisture and maturity levels, but without any change in the genotype. The following observations and size descriptions are based on two-year-old grown in a full-sun display garden of a nursery in Zeeland, Michigan.

Botanical classification: *Veronica spicata;*

Parentage: The parent is 'Purple Leia';

Propagation: The plant roots from cuttings in about 2 weeks and finishes to flowering in a 3.8-liter container in 8 to 10 weeks following a vernalization period of about 8 weeks;

Roots: Fibrous; heavily branching; color nearest RHS NN155B;

Plant habit: Hardy herbaceous perennial; compact; with about 20 stems; main stems branching in distal portion; to about 70 cm tall and clumping to about 55 cm wide; flowering beginning late spring in Michigan and continuing for up to 5 weeks;

Leaves: Lanceolate; simple; opposite; margin ciliolate and serrated with teeth 3 mm apart and 1 mm long; micro-puberulent adaxial and glabrous between veins abaxial, lustrous adaxial and matte abaxial; acute apex; distal leaves with attenuate base and proximal leaves with rounded base; flat; to about 11 cm long by 3 cm wide near middle, average about 8 cm long and 2.5 cm wide, decreasing in both length and width distally; about 16 leaves per stem;

Leaf color: Young expanding adaxial between RHS 145A and RHS 146D, abaxial nearest RHS 144A; mature adaxial nearest RHS NN137A, abaxial nearest RHS 138A;

Veins: Pinnate; adaxial midrib glabrate to glabrous, lateral veins glabrous; abaxial midrib costate and puberulent and lateral veins glabrous to glabrate;

Vein color: Adaxial midrib and proximal lateral veins nearest RHS 146C; abaxial midrib nearest RHS 146D with lateral veins nearest RHS 137B;

Petiole: Simple; concavo-convex; glabrous adaxial and abaxial; margin micro-ciliolate; base slightly clasping; to about 12 mm long and 5 mm wide at base, decreasing distally; average about 6 mm long and 3.5 mm wide;

Petiole color: Adaxial nearest RHS 146B; abaxial edges nearest RHS 137C and midrib nearest RHS 146D;

Stem: Cylindrical; puberulent; to about 45 cm long before flowers, diameter about 3 mm at base; color nearest RHS 146C;

Internodes: About 12 below flowers; average about 3.8 cm apart; node color nearest RHS 138A;

Inflorescence: Axillary and heavily branched lateral upright racemes; flowering portion to about 24.5 cm long, about 20 cm across with up to six lateral branches per stem, and central raceme about 18 mm wide; to about 550 flowers per center stem, to 330 flowers per lateral branch, and about 1400 per branched peduncle;

Flower bud one to two days prior to opening: Convolute; oblong; rounded base and apex; glabrous; about 4 mm long and 2 mm diameter;

Flower bud color one to two days prior to opening: Exposed petals nearest RHS 73A with calyxes nearest RHS 138A;

Flowers: Zygomorphic; campanulate; perfect, complete; about 6 mm across and about 8 mm long to exserted anthers; corolla about 6 mm tall and 6 mm wide; corolla tube fused in basal 2 mm and 1.7 mm diameter near base; flowers persist individually for 4 to 6 days whether on the plant or cut; petals self-cleaning, sepals and style persistent; attitude outwardly;

Flower fragrance: Not detectible;

Flower timing: Late spring and continuing for 12 to 14 weeks;

Petals: Four; one slightly larger petal above, two on either side, one slightly smaller below; rounded apices; entire; glabrous adaxial and abaxial except basal 2 mm adaxial of fused tube with pubescent tuft; fused in basal 2 mm; larger top and side petals about 4.5 mm long by 6 mm wide, smaller lower petal about 6 mm long and 3.5 mm wide;

Petal color: When first open abaxial and adaxial nearest RHS 72D lightening to between RHS 75D and RHS 75C; corolla tube base nearest RHS NN155D; adaxial tuft of hairs nearest RHS NN155D;

Androecium:

*Filaments.*—Two; divergent; glabrous; epipetalous in proximal 1 mm; to about 8 mm long by 0.3 mm diameter; color RHS N74B lightening to nearest RHS NN155D.

*Anther.*—Dorsifixed, longitudinal; ellipsoidal; with acute rounded becoming acute, base rounded; about 2 mm long and 1 mm wide; color prior to pollen dehiscence nearest RHS N77B, nearest RHS 202A dorsally RHS 83A after pollen dehiscence.

*Pollen*.—Abundant, globose, less than 0.1 mm; nearest RHS 18D.

Gynoecium: One, superior; exserted; persists after petal drop;

*Style*.—Cylindrical; straight; attitude outwardly to slightly drooping; about 6 mm long by 0.5 mm; color nearest RHS NN74D.

*Stigma*.—Globose; about 0.3 mm in diameter; color RHS NN78B.

*Ovary*.—Globose to ellipsoid; about 1.2 mm long and 1 mm across; color nearest RHS 146D.

Calyx: Campanulate; 2 mm long and 2.5 mm diameter;

Sepals: Four; lanceolate; acute apex; basal 1.5 mm fused forming campanulate calyx; margin entire, micro-ciliolate; adaxial dull and glabrous; abaxial microscopically puberulent; to about 2.5 mm long and 1 mm wide;

Sepal color: Adaxial nearest RHS 138A, abaxial nearest RHS 137A;

Peduncle: About 18 per plant; heavily-branched raceme; strong, virgate, branched at upper nodes; cylindrical; pubescent distally and glabrescent proximally;

Peduncle color: Nearest RHS 146C;

Pedicel: Rigid; cylindrical; micro-puberulent; about 1.7 mm long and 0.5 mm wide, attitude semi-upright;

Pedicel color: Nearest RHS 138B;

Bract: One; subtending each flower; linear; narrowly acute apex; sessile attenuate base; margin entire; glabrous adaxial and abaxial; proximal bracts about 15 mm long and 22 mm wide and decreasing distally to about 3 mm long and about 0.8 mm wide;

Bract color: Nearest RHS 139A adaxial and abaxial nearest RHS 137A;

Fruit: Ellipsoidal dehiscent capsule; round apex; rounded base; glabrous; to about 3 mm tall and 2 mm diameter; color at maturity between RHS 199D and RHS N200D;

Seed: Slightly flattened ellipsoidal; about 0.7 mm long, 0.5 mm across, and 0.3 mm thick; color between RHS 200C and RHS 200D;

Growth: The new plant grows best with plenty of moisture and adequate drainage but is able to tolerate some drought when mature.

Hardiness: Hardiness at least from USDA zone 4 through 8.

Disease and pest resistance: Disease and pest resistance and susceptibility beyond what is typical of that of other Spike Speedwell has not been observed.

I claim:

1. A new and distinct cultivar of *Veronica* plant named 'Jedi Gem' as herein described and illustrated.

* * * * *